(12) United States Patent
Cohen

(10) Patent No.: US 6,267,778 B1
(45) Date of Patent: Jul. 31, 2001

(54) PACING SYSTEMS FOR TREATING FUNCTIONAL VENTRICULAR CONDUCTION ABNORMALITIES OF INTRINSIC ORIGIN

(76) Inventor: Fred Michael Cohen, 2601 E. Vogel Ave., Phoenix, AZ (US) 85028

( * ) Notice: Subject to any disclaimer, the term of this patent is extended or adjusted under 35 U.S.C. 154(b) by 0 days.

(21) Appl. No.: 09/290,097

(22) Filed: Apr. 12, 1999

(51) Int. Cl.⁷ .................................................. A61N 1/362
(52) U.S. Cl. .......................................................... 607/9
(58) Field of Search .................. 607/9, 25, 26; 600/516, 517, 521

(56) References Cited

U.S. PATENT DOCUMENTS

| | | |
|---|---|---|
| 3,893,461 | 7/1975 | Preston . |
| 4,088,149 | 5/1978 | Rockland et al. . |
| 4,126,139 | 11/1978 | Walters et al. . |
| 4,444,195 | 4/1984 | Gold . |
| 4,554,922 | 11/1985 | Prystokowsky et al. . |
| 4,628,934 | 12/1986 | Ponndorf et al. . |
| 4,787,389 | 11/1988 | Tarjan . |
| 4,928,688 | 5/1990 | Mower . |
| 4,967,749 | 11/1990 | Cohen . |
| 5,018,523 | 5/1991 | Bach, Jr. et al. . |
| 5,312,445 | * 5/1994 | Nappholz et al. ................... 607/9 |
| 5,609,158 | * 3/1997 | Chan . |

FOREIGN PATENT DOCUMENTS 0030897   6/1981   (EP) .

* cited by examiner

*Primary Examiner*—Scott M. Getzow
(74) *Attorney, Agent, or Firm*—Parsons & Goltry; Robert A. Parsons; Michael W. Goltry

(57) ABSTRACT

Therapeutic implantable cardiac pacing systems incorporating electrocardiographic acquisition and QRS discrimination circuitry, for the purpose of ventricular pacing during wide QRS complexes of intrinsic origin, in order to narrow the QRS complex. Resultant narrowing of the QRS complex increases coronary artery flow and electrode position is employed to improve ventricular motion in the treatment of functional ventricular abnormalities caused by wide QRS complexes.

13 Claims, 5 Drawing Sheets

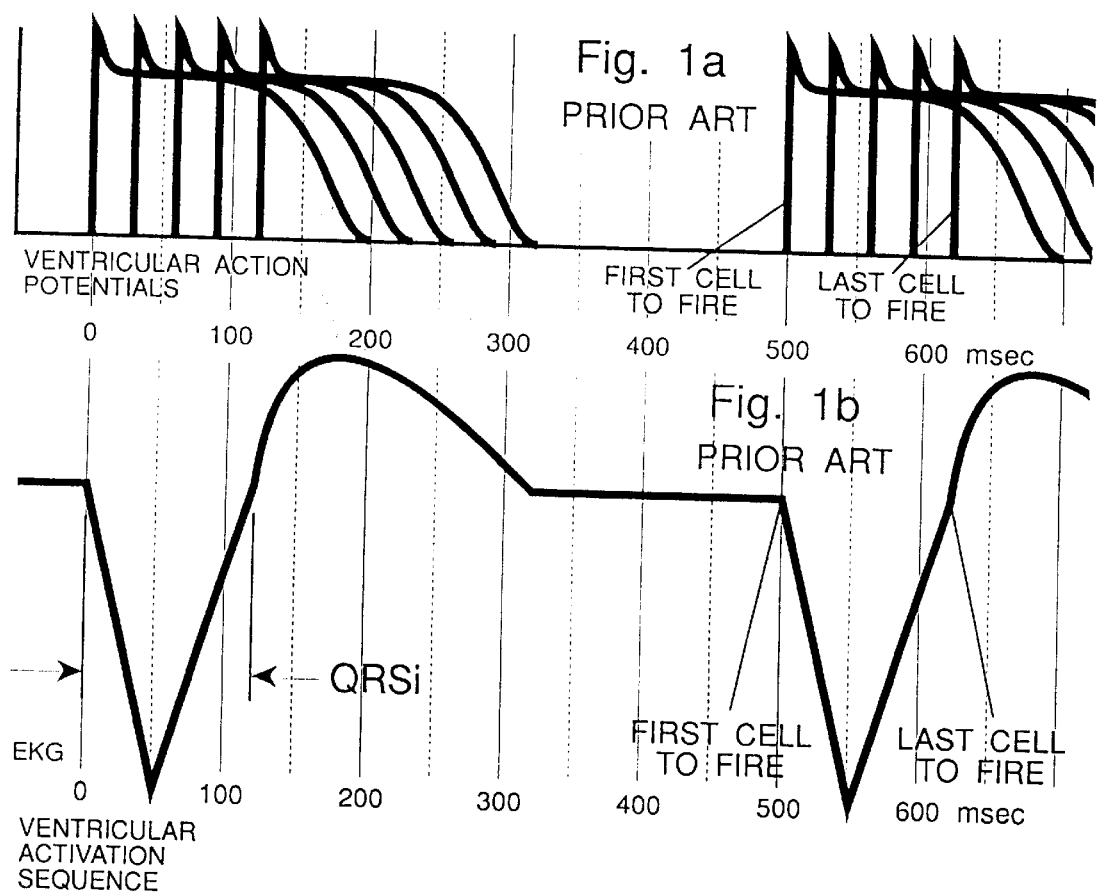
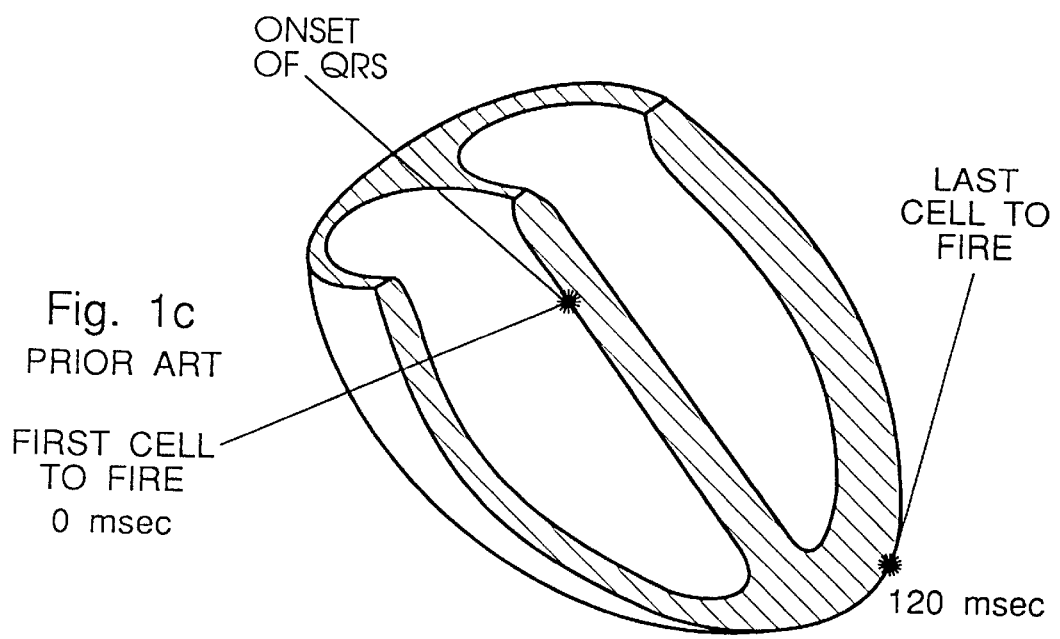

PROPAGATION OF
VENTRICULAR ACTIVATION
- FROM INTRINSIC ORIGIN

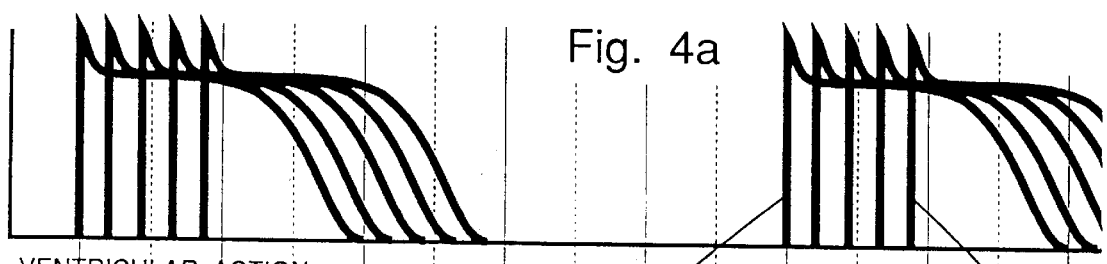
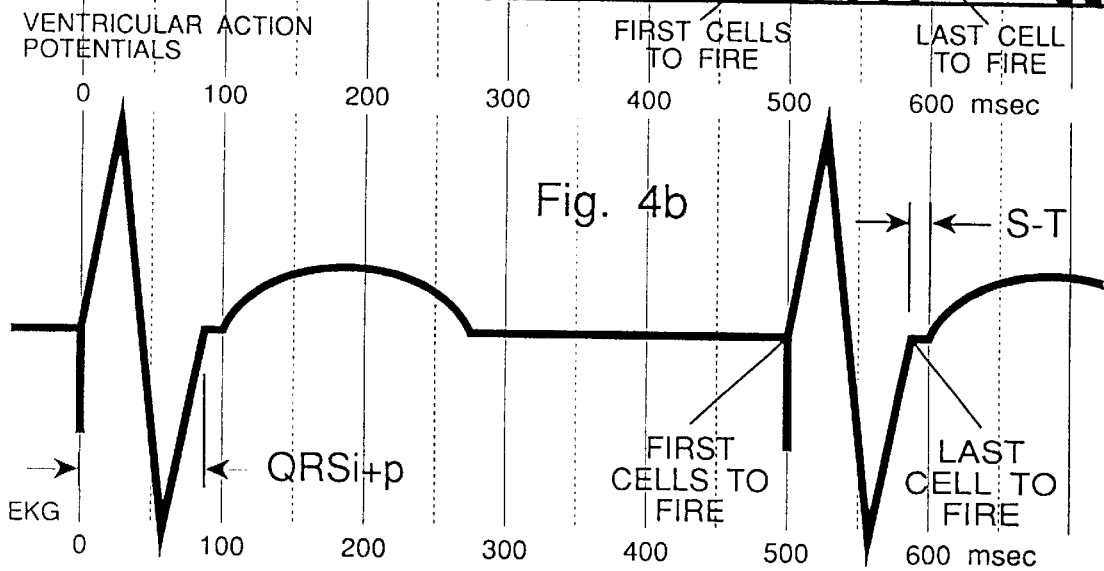
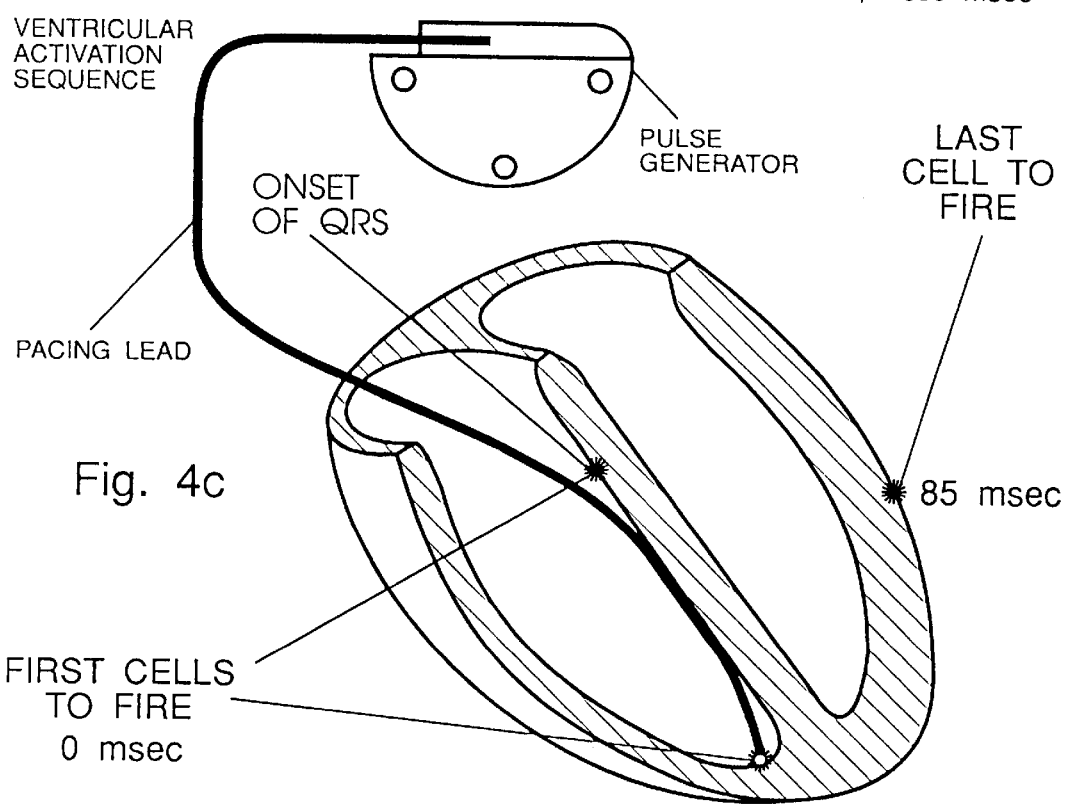

PROPAGATION OF
VENTRICULAR ACTIVATION
- FROM INTRINSIC ORIGIN
AND VENTRICULAR PACING

PACING SYSTEMS FOR TREATING FUNCTIONAL VENTRICULAR CONDUCTION ABNORMALITIES OF INTRINSIC ORIGIN

CROSS-REFERENCE TO RELATED APPLICATIONS

Not Applicable

STATEMENT REGARDING FEDERALLY SPONSORED RESEARCH OR DEVELOPMENT

Not applicable

REFERENCE TO A MICROFICHE APPENDIX

Not Applicable

BACKGROUND OF THE INVENTION

This invention relates generally to medicine and more specifically to improved cardiac pacing systems including methods of pacing and sensing in the treatment of cardiac disease. Reference is hereby made to my U.S. Pat. Nos. 5,174,289 and 5,267,560, which are incorporated herein by reference. These patents define terms that will be used herein, describe limitations of previous pacing systems, and contain prior art and classification information which may be applicable to this invention. This invention will describe additional systems and methods for controlling the ventricular activation sequence in the treatment of patients with wide QRS complexes of intrinsic origin.

BRIEF SUMMARY OF THE INVENTION

One object of the present invention is to provide pacing methods and systems which have the capability of improving ventricular function both in the duration of its contraction (by narrowing QRS duration) and the control of ventricular wall and septal motion.

Another object of the present invention is to provide methods and systems for detecting the onset of the QRS complex by means of acquiring and analyzing an electrocardiogram, and employing said QRS onset to trigger at least one ventricular pacing impulse.

According to the present invention at least one pacing electrode is triggered to stimulate the ventricular muscle by the detected onset of a QRS complex of intrinsic origin, either simultaneously or at a delayed interval or intervals.

Reference is hereby made to my previous written and illustrated description which was filed under the Disclosure Document Program on Jan. 6, 1998 and assigned Disclosure Document No. 430365, which is incorporated by reference herein.

The foregoing and other objects, features and advantages of the invention will be apparent from the following, more particular description of the preferred embodiment of the invention, as illustrated in the accompanying drawings.

BRIEF DESCRIPTION OF THE SEVERAL VIEWS OF THE DRAWING

FIG. 1a illustrates the ventricular action potential distribution of a wide duration QRS complex of intrinsic origin where initial activation occurs high on the right ventricular septum.

FIG. 1b illustrates the electrocardiogram of a wide duration QRS complex of intrinsic origin where initial activation occurs high on the right ventricular septum.

FIG. 1c illustrates the sequence of cell firing, within a ventricular cross section, of a wide duration QRS complex of intrinsic origin where initial activation occurs high on the right ventricular septum;

FIG. 4a illustrates the ventricular action potential distribution of a QRS complex of intrinsic origin high on the right ventricular septum (as in 1a), where a right ventricular apical area is activated, by a pacing system, simultaneous with the onset of the QRS complex.

FIG. 4b illustrates the electrocardiogram of a QRS complex of intrinsic origin high on the right ventricular septum (as in 1b), where a right ventricular apical area is activated, by a pacing system, simultaneous with the onset of the QRS complex.

FIG. 4c illustrates the sequence of cell firing, within a ventricular cross section, of a QRS complex of intrinsic origin high on the right ventricular septum (as in 1c), where a right ventricular apical area is activated, by a pacing system, simultaneous with the onset of the QRS complex;

DETAILED DESCRIPTION OF THE INVENTION

Figure 2:
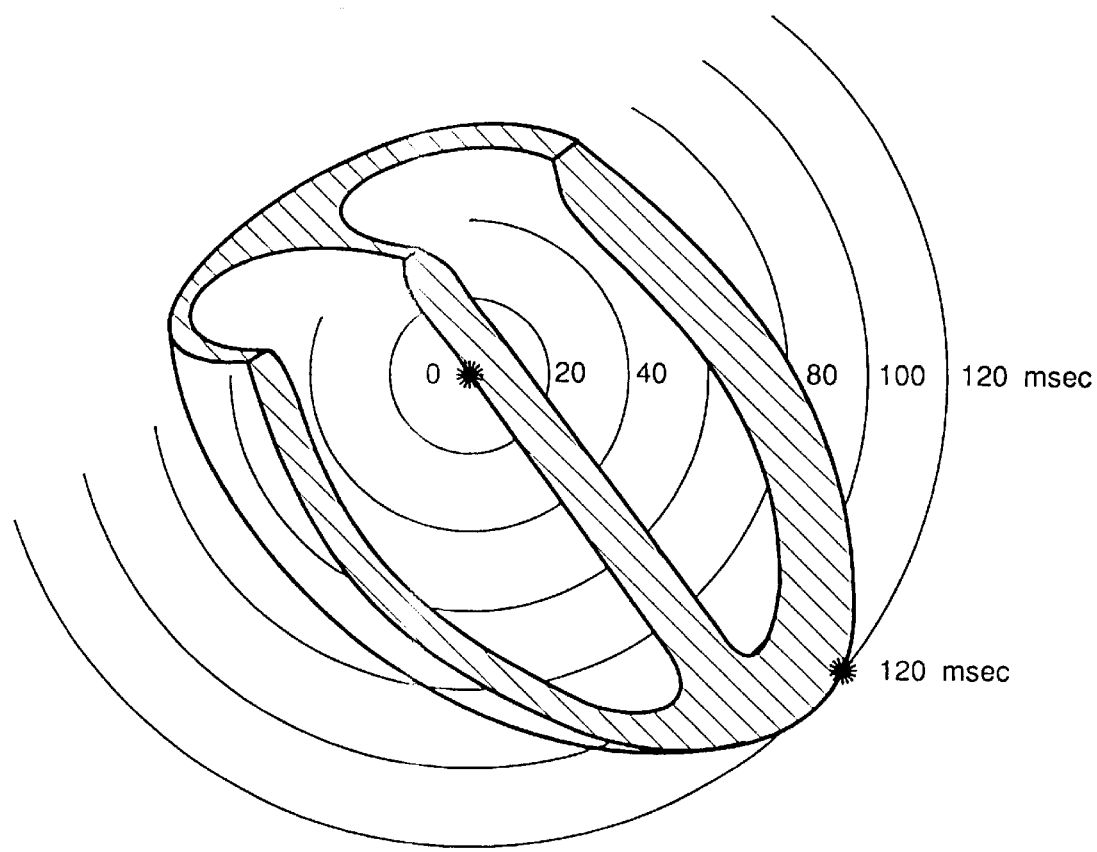
FIG. 2 illustrates the propagation of activation, within a ventricular cross section, during the wide duration QRS complex of intrinsic origin where initial activation occurs high on the right ventricular septum, as previously illustrated in FIGS. 1a–1c.

This invention will describe novel methods and apparatus to shorten the QRS complex in patients who exhibit wide QRS complexes of intrinsic origin. Wide QRS complexes of intrinsic origin may begin at any ventricular location and may be caused by varying degrees of bundle branch block, premature ventricular contractions, myocardial infarction or other factors. FIGS. 1a, 1b & 1c represent, the ventricular action potential sequence, the electrocardiogram and the point of initial ventricular activation, high on the right ventricular septum, which may occur as a result of a premature ventricular contraction. FIG. 2 illustrates the propagation of ventricular activation produced by the intrinsic origin described in FIG. 1c, according to the approximations and conditions previously described for the patient in U.S. Pat. Nos. 5,174,289 and 5,267,560. FIG. 1b depicts a QRSi equal to 120 msec which is the QRS interval of intrinsic origin in this example.

As can be seen from FIG. 1c, the intrinsic origin of a wide QRS interval may not be easily accessible by previously described methods and apparatus (U.S. Pat. Nos. 5,174,289 and 5,267,560) as they require placement of a sensing electrode at or near the intrinsic origin, in order to obtain the most substantial shortening of a QRS complex. It may be difficult to position an electrode high on the right ventricular septum, especially with a single lead, and left ventricular electrode placement exposes the patient to the additional risks of thoracotomy, coronary sinus thrombosis or arterial cannulation. Thus in certain cases it is desirable to detect the onset of the QRS interval without the placement of electrodes.

Figure 3:
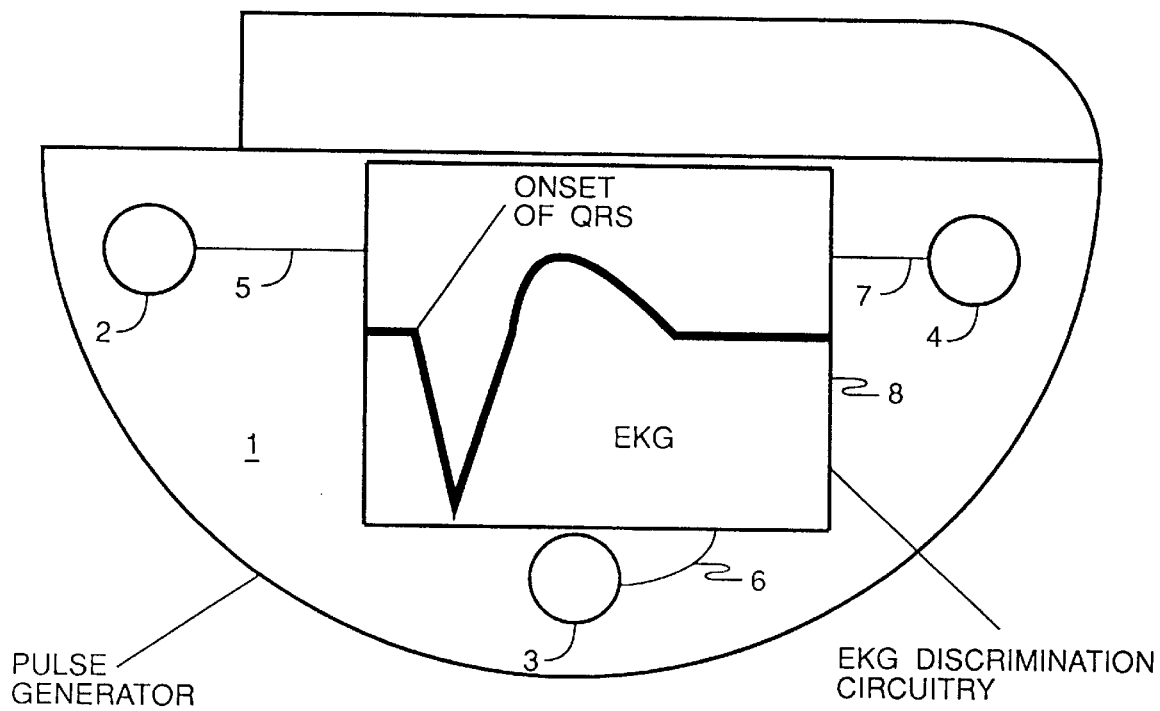
FIG. 3 illustrates an implantable pulse generator with electrodes for monitoring an electrocardiogram that is analyzed by discrimination circuitry for determining the onset of the QRS duration.

FIG. 3 illustrates an implantable pulse generator 1 with electrodes 2, 3 and 4 attached, for the purpose of acquiring an electrocardiogram (EKG). Electrodes 2, 3 and 4 are insulated from the pulse generator case and are electrically connected to discrimination circuitry 8, which may include an amplifier, by means of electrical connections 5, 6 and 7. Electrical connections 5, 6 and 7 enter the pulse generator by means of well known feedthrough connections, to maintain a hermetic seal of the pulse generator circuitry. Electrodes 2, 3 and 4 may also be located remote from the pulse generator to obtain a larger signal and electrical connections 5, 6 and 7 may enter the pulse generator through a single feedthrough. Additional electrodes may also be employed to produce additional EKG channels which may be of value in producing an accurate determination of the QRS onset and eliminating baseline wander. Standard EKG recorders utilize four electrodes to display three channels, etc.

Once an EKG is obtained, circuitry similar to the well known discrimination circuitry, as employed in present EKG recorders which analyze QRS morphology, is employed to determine the onset of the QRS duration. Under conditions of constant heart rate the discrimination circuitry could anticipate the actual initial QRS deflection based upon acquired data, but this method would not be suitable under conditions of varying rate which occurs naturally. Thus this circuitry will be most useful when analyzing each beat in real time and discrimination of QRS onset may be made by means of rate of voltage change with respect to time, direction of deflection, amplitude or their various combinations and ranges that are appropriate for QRS onset detection in an individual patient. Within a real time method of operation the onset of the QRS interval would actually comprise a relatively short time interval beginning with initial QRS deflection and terminating when the discrimination circuitry determines that a QRS is detected. FIGS. 1c, 3 and 4c show the "onset of QRS" as a point in time with the understanding that it could actually be a relatively short time interval depending upon the method in which it is detected by the discrimination circuitry 8.

In an implantable system, once an EKG is obtained, well known memory and telemetry systems may be employed to store EKG data over time and display its history as an aid in diagnosis of heart disease. Real time display of the EKG is also possible with these systems.

Well known pacemaker telemetry systems may be used to non-invasively program the rate of voltage change with respect to time, direction of deflection or amplitude at which a QRS onset is most effectively detected in a particular patient. Combinations and ranges, of rates of voltage change with respect to time, directions of deflection or amplitudes may be programmed in order to enable the pulse generator to respond to various wide QRS complexes in an individual patient, produced for example, as a result of complete left bundle branch block and various premature ventricular contractions.

Once the onset of the QRS complex is determined, this signal may be employed in otherwise well known pulse generator circuitry to trigger at least one simultaneous or delayed pacing impulse delivered to at least one ventricular electrode that is placed to shorten the QRS duration and produce a more normal ventricular wall motion according to the methods described in U.S. Pat. Nos. 5,174,289 and 5,267,560. One method is to employ a VVT or VVTR pulse generator system modified so that the signal it detects is the onset of the QRS complex rather than an intrinsic ventricular signal at a ventricular electrode. Thus a ventricular pacing impulse would be delivered to the ventricular electrode simultaneous with the detection of the QRS onset and in the absence of a detected QRS onset within a predetermined time interval.

Figure 5:
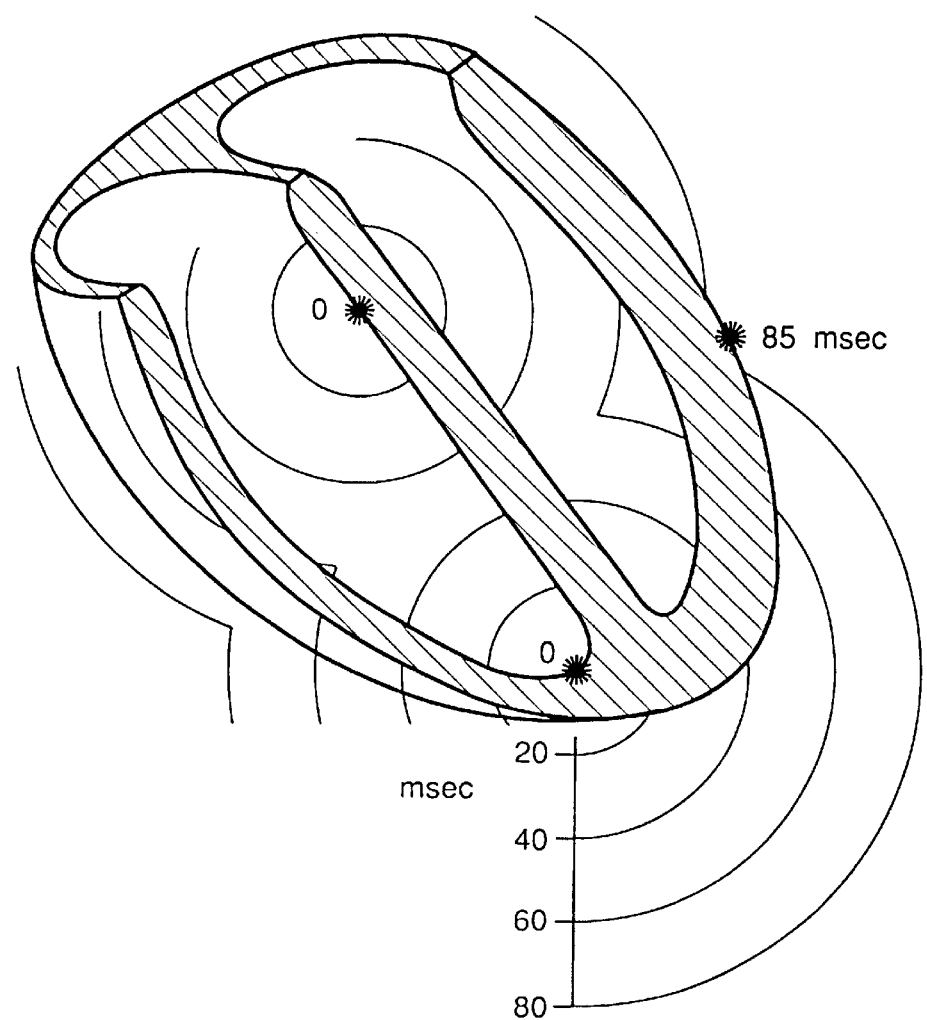
FIG. 5 illustrates the propagation of activation, within a ventricular cross section, during a QRS complex of intrinsic origin high on the right ventricular septum (as in 2), where a right ventricular apical area is activated, by a pacing system simultaneous with the onset of the QRS complex, as previously illustrated in FIGS. 4a–4c.

Another method of pacing is essentially similar to that of a "VDD" or "VDDR" pacemaker, adapted for ventricular use as described in U.S. Pat. Nos. 5,174,289 and 5,267,560, modified so that the first signal it detects is the onset of the QRS complex rather than a signal from a ventricular electrode or electrodes, thus eliminating the necessity of these electrode(s) and their positioning near a ventricular area of initial activation. In this configuration, if a QRS onset was not detected, for example due to inappropriate settings, the pacing impulse would be inhibited by intrinsic ventricular activity at the electrode during the predetermined interval. Also in this pacing system, the absence of ventricular electrical activity at the electrode during the predetermined interval and the absence of a detected QRS onset during the predetermined interval, would cause a ventricular pacing impulse to be delivered at expiration of the predetermined interval. FIG. 4c depicts a well known conventional pacing lead connected to the pulse generator 1, with its pacing electrode placed at the right ventricular apex in order to produce a more normal ventricular wall motion and shorter QRS interval when pacing simultaneous with the onset of the QRS complex, as compared to the same patient without pacing depicted in FIG. 1c. FIGS. 1a and 1b depict the resultant action potential distribution and electrocardiogram respectively when right ventricular apical pacing occurs simultaneous with the onset of the QRS complex, based upon the approximations and conditions of the patient described in U.S. Pat. Nos. 5,174,289 and 5,267,560. FIG. 5 depicts the propagation of ventricular activation when right ventricular apical pacing occurs simultaneous with the onset of the QRS complex, according to the above approximations and conditions. FIG. 4b depicts a QRSi+p equal to 85 msec which is the QRS interval which results from the onset of a QRS complex of intrinsic origin (as depicted in 1c), simultaneous with paced stimulation at the right ventricular apex. Therefore the patient will benefit from a 35 msec shorter QRS interval (QRSi−QRSi+p=120−85 msec). A pacing impulse that randomly occurs during a QRS complex is commonly referred to in the art as ventricular fusion. Pacing systems of this invention will provide apparatus and methods to produce controllable and predictable ventricular fusion for the purpose of decreasing wide QRS durations of intrinsic origin.

It should be understood that in addition to pacing from a single point, the methods and apparatus described in U.S. Pat. Nos. 5,174,289 and 5,267,560 for pacing and sensing at multiple points may also be employed to further decrease QRS duration in a pacing system which acquires and analyzes an EKG to produce ventricular fusion. It should also be understood that a premature ventricular contraction may have an apical origin and in this circumstance a mid-septal electrode would be of greatest value in shortening the QRS duration while maintaining a normal ventricular wall motion. Thus in patients with multi-focal premature ventricular contractions multiple pacing electrode locations may be of value shortening QRS duration and producing a more normal ventricular wall motion, with selection of the best electrode(s) to pace through being made on the basis of QRS onset morphology, with stimulation occurring at selected electrodes based upon the origin of the QRS. Alternatively, multiple electrode stimulation may be employed, for example at apical and mid-septal positions in response to the QRS onset.

Certain patients may exhibit narrow QRS complexes of intrinsic origin in addition to wide QRS complexes of intrinsic origin as, for example, may occur during intermittent complete left bundle branch block or premature ventricular contractions. In these cases, it is not desirable to deliver a pacing impulse into a narrow QRS complex due to the fact that this pacing impulse may serve to widen an otherwise narrow QRS complex. In the event the discrimination circuitry is able to distinguish between the onset of a narrow intrinsic QRS complex and the onset of a wide intrinsic QRS complex, by analysis of their morphologies, the pulse generator may be programmed to deliver pacing impulses only into a wide complex. An alternative method, in these patients, would be to incorporate a delay interval between the detected onset of an intrinsic QRS complex and the deliverance of a pacing impulse. The pulse generator would be inhibited by intrinsic ventricular electrical activity at the pacing electrode during the delay interval, as is well known in the art. Therefore intrinsic electrical activity occurring at the electrode during the delay period would result from a narrow intrinsic QRS complex while the absence of electrical activity at the electrode during the delay interval would result from a wider QRS complex, into which the pulse generator would deliver a pacing impulse at expiration of the delay interval. When multiple electrodes are employed, more than one delay interval may be programmed between the onset of the QRS and the electrodes or between electrodes, according to U.S. Pat. Nos. 5,174,289 and 5,267,560.

Acquisition and discrimination of the electrocardiogram may also be employed to determine the onset of the P wave in a dual chamber (VDD) pacing system, thus eliminating the atrial sensing electrode presently used in these systems, and allowing ventricular stimulation at a delayed time interval (AV interval).

I claim:

1. Implantable cardiac electrical apparatus comprising:

means for acquiring, storing and displaying the electrocardiogram of a patient;

second means for detecting the onset of the QRS complex of intrinsic origin and differentiating between multiple QRS complexes of varying morphologies; and third means for discriminating between the onsets of narrow and wide QRS complex morphologies of intrinsic origin.

2. Apparatus according to claim 1 additionally comprising a pacing system for employing said onset of a narrow QRS complex within a predetermined time interval to inhibit stimulation of the ventricular muscle at, at least one ventricular location, within said predetermined time interval; for employing said onset of a wide QRS complex within said predetermined time interval to stimulate the ventricular muscle at, at least one said ventricular location, simultaneous with said onset of a wide QRS complex and employing the absence of said onset of any QRS complex within said predetermined time interval to stimulate the ventricles at, at least one said ventricular location.

3. A method for improving the ventricular function of the heart of a patient comprising the steps of:

(a) acquiring the electrocardiogram (EKG) of a patient;

(b) electronically analyzing said EKG to determine the onset of the QRS complex of intrinsic origin;

(c) placing at least one electrode to stimulate the ventricular muscle at, at least one location selected to shorten a wide QRS complex of intrinsic origin upon ventricular stimulation simultaneous with said onset of the QRS complex;

(d) electrically connecting at least one of said electrodes to a pacing system;

(e) employing said onset of the QRS complex within a predetermined time interval to stimulate the ventricular muscle at, at least one said ventricular location, simultaneous with said onset of the QRS complex and employing the absence of said onset of the QRS complex within said predetermined time interval to stimulate the ventricular muscle at, at least one said ventricular location.

4. The method of claim 3 wherein ventricular electrical activity at, at least one said ventricular electrode within said predetermined time interval inhibits the deliverance of said ventricular stimulation to at least one electrode.

5. The method of claim 4 wherein there is a delay interval between said onset of the QRS interval and said ventricular stimulation of at least one electrode.

6. The method of claim 5 wherein at least one said ventricular stimulation is inhibited by intrinsic electrical activity occurring at, at least one said electrode during said delay interval and predetermined interval.

7. The method of claim 3 wherein at least one said electrode is located on the endocardial surface of a ventricular chamber.

8. Cardiac electrical stimulation apparatus comprising; first means for acquiring the electrocardiogram of a patient; second means responsive to said first means for determining the onset of the QRS complex; and third means having output means and responsive to said second means for providing at least one stimulating impulse to at least one ventricular location simultaneous with said onset of the QRS complex within a predetermined time interval and providing at least one stimulating impulse to at least one said ventricular location in the absence of said onset of the QRS complex within said predetermined time interval.

9. Apparatus according to claim 8 additionally comprising fourth means, to which said third means is responsive, for providing inhibition of at least one said stimulating impulse to at least one said ventricular location upon the detection of intrinsic ventricular activity at, at least one said ventricular location within said predetermined time interval.

10. Apparatus according to claim 9 additionally comprising fifth means, to which said third means is responsive, for providing a programmable delay interval between said onset of the QRS complex and at least one said stimulating impulse to at least one said ventricular location.

11. Apparatus according to claim 10 wherein the fourth is also means for sensing at least one ventricular depolarization of intrinsic origin and inhibiting at least one said stimulating impulse upon the occurrence of said ventricular depolarization of intrinsic origin during said delay interval and said predetermined interval.

12. Apparatus according to claim 11 additionally comprising sixth means for sensing at least one ventricular depolarization of intrinsic origin and inhibiting at least one said stimulating impulse upon the occurrence of said ventricular depolarization of intrinsic origin during said delay interval.

13. A method for improving the atrial and ventricular function of the heart of a patient comprising the steps of:

(a) acquiring the electrocardiogram (EKG) of a patient;

(b) electronically analyzing said EKG to determine the onset of the P wave of intrinsic origin;

(c) placing at least one electrode to stimulate the ventricular muscle;

(d) electrically connecting at least one of said ventricular electrodes to a pacing system;

(e) employing said onset of the P wave within a predetermined time interval to stimulate the ventricular muscle at, at least one said ventricular location, at a programmed delay interval from said onset of the P wave, in the absence of ventricular electrical activity at, at least one electrode during said predetermined interval and employing the absence of said onset of the P wave within said predetermined time interval to stimulate the ventricular muscle at, at least one said ventricular location at expiration of said predetermined interval.

* * * * *